United States Patent [19]

Pennatto

[11] Patent Number: 5,171,530
[45] Date of Patent: Dec. 15, 1992

[54] VIAL LOCATOR AND SENSOR

[75] Inventor: Samson Pennatto, Danbury, Conn.

[73] Assignee: The Perkin-Elmer Corporation, Norwalk, Conn.

[21] Appl. No.: 803,669

[22] Filed: Dec. 3, 1991

Related U.S. Application Data

[63] Continuation of Ser. No. 730,034, Jul. 12, 1991, abandoned, which is a continuation of Ser. No. 488,569, Feb. 28, 1990, abandoned.

[51] Int. Cl.$^5$ .............................................. G01N 35/00
[52] U.S. Cl. ........................................ 422/63; 422/64; 436/47; 436/54; 73/864.21; 73/864.24
[58] Field of Search ................... 422/64, 65, 63, 62, 422/67, 100; 436/47, 54; 73/864.14, 864.21, 864.23, 864.24, 864.25

[56] References Cited

U.S. PATENT DOCUMENTS

| | | | |
|---|---|---|---|
| 3,549,330 | 12/1970 | Junger et al. | 422/64 |
| 3,748,911 | 7/1973 | Rousselet et al. | 73/864.25 |
| 3,991,627 | 11/1976 | Laird et al. | 73/864.23 |
| 4,296,070 | 10/1981 | Montalto et al. | 422/65 |
| 4,445,280 | 6/1984 | Shinohara et al. | 422/64 |
| 4,478,095 | 10/1984 | Bradley et al. | 73/864.21 |
| 4,517,851 | 5/1985 | Tice | 422/64 |
| 4,539,855 | 9/1985 | Jacobs | 73/864.25 |
| 4,713,974 | 12/1987 | Stone | 73/864.21 |
| 4,794,085 | 12/1988 | Jessop et al. | 436/54 |
| 4,928,539 | 5/1990 | Champseix et al. | 422/64 X |
| 5,012,845 | 5/1991 | Averette | 422/63 X |

FOREIGN PATENT DOCUMENTS 2137526  10/1984  United Kingdom .

Primary Examiner—James C. Housel
Assistant Examiner—Long V. Le
Attorney, Agent, or Firm—Edwin T. Grimes

[57] ABSTRACT

An analytical instrument sample vial positioning and sensor device. A radius or cone-shaped body portion extending below a surface contacts a loosely held sample vial having a flexible septum thereon. The shaped body portion is biased downward resulting in the relative movement between the sample vial and shaped body portion tending to center the flexible septum under the shaped body. A longitudinal bore extending through the shaped body permits the insertion of a syringe needle for the removal of a sample to be analyzed. The pre-positioning of the sample vial presents syringe needles from being bent or broken due to inappropriate alignment with respect to the septum. A sensor is incorporated with the shaped body to detect the presence or absence of a sample vial.

11 Claims, 2 Drawing Sheets

5,171,530

VIAL LOCATOR AND SENSOR

This application is a continuation of application Ser. No. 07/730,034 filed Jul. 12, 1991, now abandoned, which in turn is a continuation of application Ser. No. 07/488,569 filed Feb. 28, 1990, now abandoned.

FIELD OF THE INVENTION

This invention relates generally to the automated locating of sample vials, and more particularly to automatically positioning a sample vial loosely placed in a carousel for use in automated analytical instruments, such as a gas chromatograph.

BACKGROUND OF THE INVENTION

In analyzing materials a sealed vial containing a prepared sample is often used. To analyze a sample a portion is removed from the sealed vial, which has a septum, with a syringe. The syringe is then used to inject the sample into an analytical instrument such as a gas chromatograph. In the past this process has been done manually. However, there have been advances in automating this process. In one automatization technique the sample vials are loosely placed in a carousel having a plurality of holes. The rotating carousel can then position one of the sample vials under an automated syringe. The vials are typically manufactured with a rigid cap having a small central opening of approximately 3/16 inches in diameter disclosing a septum. The vials are usually placed within the carousel manually. For ease of insertion this requires that they be loosely held. This in combination with the range of tolerances necessary for the economical manufacture of sample vials results in the location of the septum to vary over a relatively large range.

In an automated system the precise location of the various components is necessary. In attempts to automate a vial sampling technique in analytical instruments, the positioning of the septum so that a needle of a syringe can be inserted has proven to be a problem. Without a mechanism for positioning the septum under the syringe needle, the syringe needle is often broken or bent. When the septum is not positioned correctly and the needle strikes the rigid cap, the needle can break or bend. Even when the septum is successfully located if the angle of incidence is too large the needle may not pierce the septum, but be deflected by it. This also results in the needle bending or breaking. This is especially true when thin needles are used as is often necessary. Conventional automated mechanisms for positioning items have proven to be too complex and bulky. Therefore, there is a need for a simple economical device for positioning a sample vial for use in analytical instruments, such as a gas chromatograph.

SUMMARY OF THE INVENTION

The present invention is directed to a vial locator and positioner for use in analytical instruments, specifically a gas chromatograph. A cone shaped or hemispherical shaped locator body is biased to extend below a surface. The shaped locator body is positioned to come into contact with a sample vial loosely held in a rotating carousel. The shaped locator body portion has a longitudinal bore through which a syringe needle can extend. As the carousel and a syringe tower are positioned the biased locator body contacts the cap and recessed septum of the vial. The coaction of the vial and shaped locator body results in the vial septum being forced under the locator body. The syringe needle can then be inserted accurately into the septum preventing the needle form being bent or broken. The shaped locator body portion also acts as a needle guide. Additionally, associated with the shaped locator body is a sensor for determining if a vial is positioned below the locator. As a result, the sample vial is simply and accurately positioned below the syringe needle by the relative motion of the rotating carousel and the syringe tower.

Accordingly, it is an object of the present invention to position a loosely held vial.

It is a further object of the present invention to guide the syringe needle preventing the needle from being bent or broken.

It is yet another object of the present invention to incorporate a simple sensor to detect the existence of a vial before attempting to withdraw a sample.

It is an advantage of the present invention that it is a simple design having no complex parts.

It is a further advantage of the present invention that the device provides a self-centering type motion based on the relative movement of the carousel and the syringe tower.

It is a feature of the present invention that a biased shaped locator is used for positioning a vial.

These and other objects, advantages, and features will become readily apparent in view of the following more detailed description.

DETAILED DESCRIPTION OF THE PREFERRED EMBODIMENTS

Figure 1:
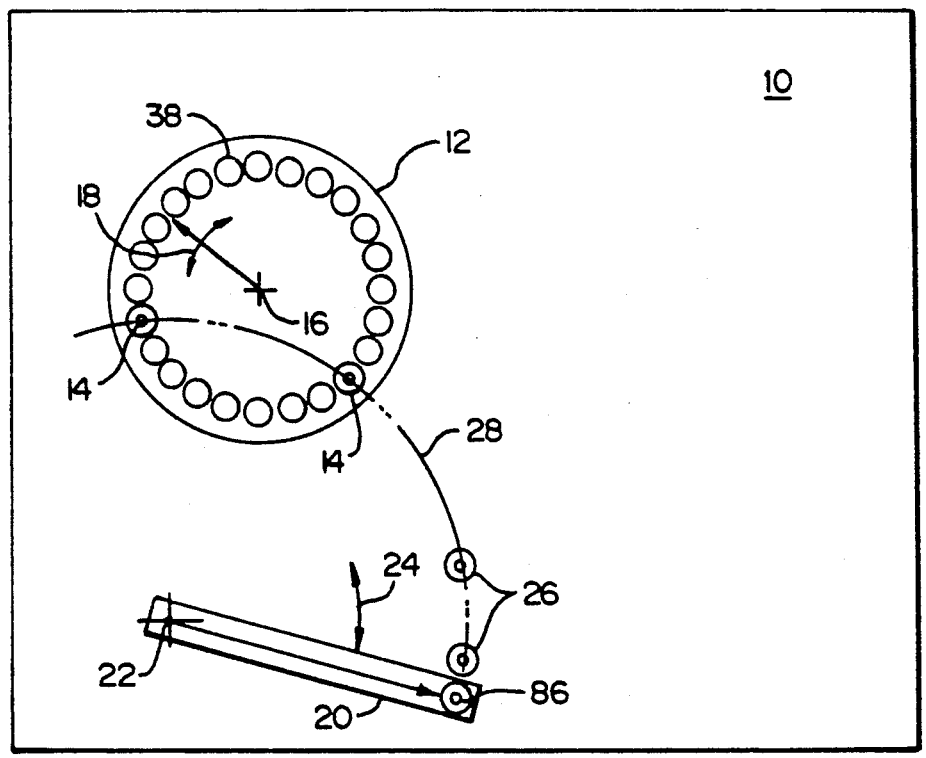
FIG. 1 is a schematic diagram of an analytical instrument system incorporating the present invention.

FIG. 1 is a schematic representation of an automated analytical instrument system incorporating the present invention. Located on a planar surface 10 is a carousel 12. Placed within carousel 12 are sample vials 14. The sample vials 14 are loosely positioned in recesses or holes 38. The carousel 12 rotates about center 16. The carousel 12 can rotate forward and backward as indicated by arrow 18. Also positioned on planar surface 10 is tower 20. The tower 20 rotates about a tower pivot 22. The tower 20 can rotate back and forth as indicated by arrow 24. Injectors 26 are located on the tower arc 28.

In operation, the analytical instrument illustrated in FIG. 1 samples any of the vials located in the carousel 12. On the tower 20 opposite the pivot 22 is positioned a syringe 86. The tower 20 pivots on pivot 22 along arc 28 positioning the syringe 86 over one of the vials 14. When the tower 20 positions the syringe 86 over one of the vials 14 a syringe needle withdraws a sample from one of the vials 14. The syringe 86 is then positioned by tower 20 over one of the injectors 26 where the sample is injected. Separate processing is then accomplished to analyze the sample. The carousel 12 is then rotated moving into position another sample contained in one of the vials 14.

Figure 2:
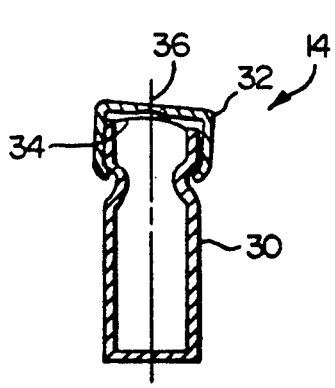
FIG. 2 is a cross-section of a sealed sample vial.

FIG. 2 illustrates one of the sample vials 14. A glass container 30 contains the sample to be analyzed. A rigid cap 32 is crimped over a pliable septum 34. The rigid cap 32 has a hole 36 therein exposing a small portion of the septum 34. It is this small portion of the septum 34 through which the syringe needle must pierce before the removal of a sample.

Figure 3:
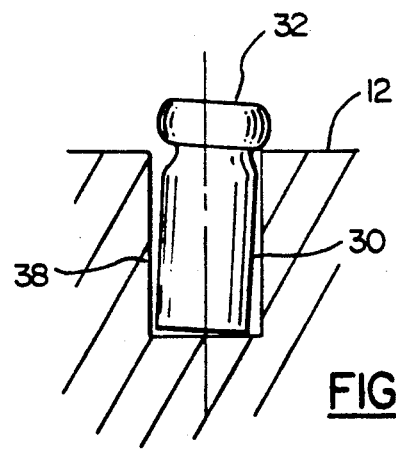
FIG. 3 diagrammatically illustrates a vial position.

FIG. 3 illustrates the position which a sample vial takes when placed in carousel 12. Carousel 12 has a plurality of recesses or holes 38 in which one of the vials 14 is placed. Recess or hole 38 is larger than the diameter of the container 30. For this reason the longitudinal axis of one of the vials 14 may be skewed with respect to the axis of the recess or hole 38. The precise position of one of the vials 14 in the carousel 12 is therefore unpredictable. This uncertainty as to the positioning of one of the vials 14 in carousel 12 is in addition to the uncertainties due to manufacturing tolerances in the positioning of the rigid cap 32 and cap hole 36 with respect to the container 30. The cap 32 can be placed off center on the container 30. Therefore, the position of the septum 34 can vary by relatively large amounts. However, the precise positioning of the syringe needle over the septum 34 exposed by the hole 36 requires the accurate positioning of the septum 34.

Figure 4:
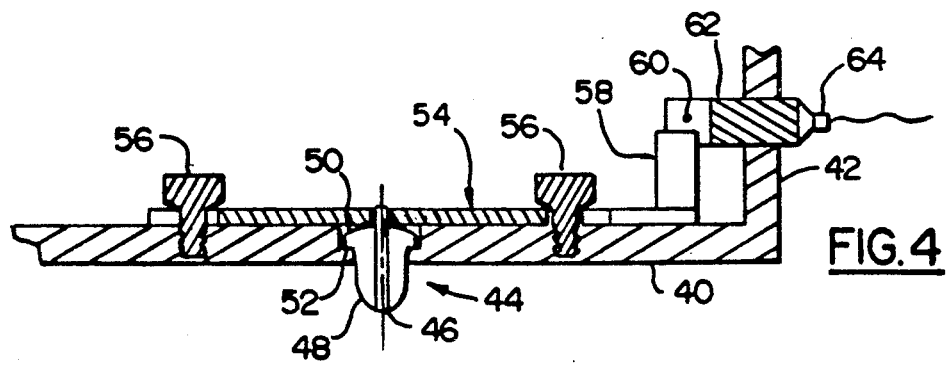
FIG. 4 is a cross-section of one embodiment of the present invention.

FIG. 4 illustrates one embodiment of the present invention. The lower portion of the tower 20 below syringe 86 illustrated in FIG. 1 is illustrated in FIG. 4. Support member 40 forms a portion of tower 20, illustrated in FIG. 1. Within support member 40 is a hole through which a shaped vial locator 44 is positioned. Vial locator 44 comprises a locator body having a radius 48. A bore 46 extends longitudinally through the vial locator 44. A ridge 50 rests on the shoulder 52 preventing the vial locator 44 from extending completely below support member 40. A leaf spring 54 rests on the top surface of ridge 50 holding the vial locator 44 in position. The vial locator 44 is biased by the leaf spring 54 into a position beneath the lower surface of support member 40. The leaf spring 54 is held in position by screws 56. Attached to the leaf spring 54 is a tab 58. Tab 58 is normally positioned below a sensor 60. Sensor 60 is attached to a sensor support 62 which in turn is connected to bracket 42 which forms a part of the support member 40. The sensor 60 can be any type of sensor, such as a mechanical switch, or an electromechanical switch, or a photodetector, for example. The electrical connector 64 is connected to the appropriate circuitry controlling other operations. One operation being the preventing of the taking of a sample if a vial is not present.

In operation, referring to FIGS. 1-4, the tower 20 swings over one of the vials 14 in carousel 12. The rigid cap 32 then strikes radius 48 on the vial locator 44. The vial locator 44 is forced upward thereby deflecting leaf spring 54. The vial locator 44 will then work itself into the hole 36 of rigid cap 32 deflecting the septum 34. In this way, one of the vials 14 is located, positioned, and centered below the bore 46. A syringe needle can then be lowered through bore 46 and septum 34.

Figure 5:
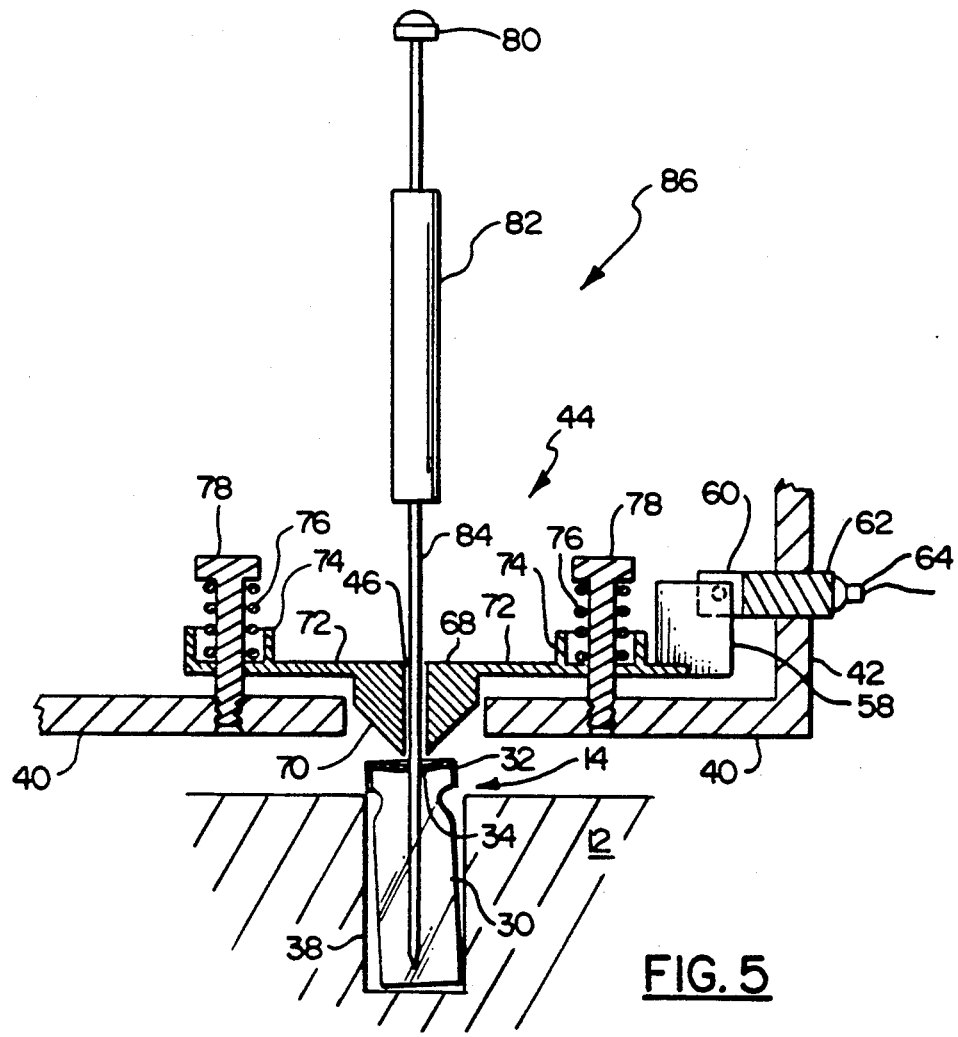
FIG. 5 is a cross-section of another embodiment of the present invention.
Figure 6:
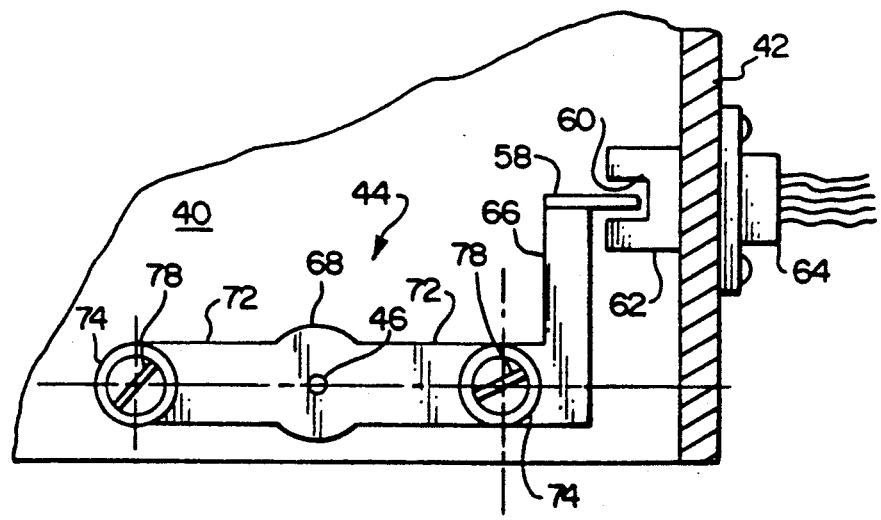
FIG. 6 is a plan view of the embodiment illustrated in FIG. 5.

FIGS. 5 and 6 illustrate a modified embodiment that uses helical spring biasing means rather than the leaf spring as illustrated in FIG. 4. The helical springs provide a greater range of vertical motion than provided by the leaf spring illustrated in FIG. 4. In FIG. 5 body portion 68 of vial locator 44 is connected to a cone 70. A cone of approximately 45 degrees has proven to work well. The body portion 68 is attached to a pair of arms 72. At the end of each arm 72, opposite the body portion 68, are a pair of spring cups 74. The spring cups 74 help retain the pair of helical springs 76. The springs 76 are retained by a pair of screws 78 which are attached to support member 40. The cone 70 is normally biased by springs 76 to extend below the surface of support member 40.

The operation of the embodiment illustrated in FIG. 5 can readily be appreciated. With reference to FIGS. 1-3 and FIG. 5, when the tower 20, containing the support member 40, moves into position over carousel 12 the cone 70 strikes the rigid cap 32 and is raised up thereby. When the septum 34 is engaged the cone 70 will lower slightly due to the biasing of springs 76 and force one of the loosely held vials 14 into position. A syringe 86 having a syringe needle 84, a syringe body 82, and a syringe plunger 80 is then automatically positioned over the locator 44. The syringe needle 84 is inserted through bore 46 and septum 34 to withdraw a sample. The sample is injected into injectors 26 for further processing by the analytical instrument. To assist in the locating and positioning of one of the vials 14 the carousel 12 can be moved back and forth.

The back and forth motion can also be sequentially reduced to further assist in centering one of the vials 14. For example, the carousel 12 can initially move 10/32 inches counterclockwise, 8/32 inches clockwise, 6/32 inches counterclockwise, 4/32 inches clockwise, 2/32 inches counterclockwise, and 1/32 inches clockwise. This may be necessary to positively locate the septum which can be as small as 3/16 inches in diameter.

FIG. 6 illustrates another feature of the present invention. When the vial locator 44 strikes one of the vials 14 and is raised upward a tab 58 connected to the vial sensor by leg 66 is also raised upward. This interferes with a sensor 60 attached to a sensor support 62. The sensor 60 can be any sensor including an electromagnetic sensor or photosensor. The signal developed thereby is transferred by an electrical connector 64 to further control the operation of the analytical instrument system. The sensor is primarily used to detect the presence or absence of one of the vials 14. If one of the vials 14 is not in position the vial locator 44 will not cause the sensor 60 to emit a signal. Control circuits can then be implemented to prevent an attempt at taking a sample which could result in damage.

It should now be appreciated that the present invention provides an advance in automated sampling techniques for use in analytical instruments, such as gas chromatographs. This advance is provided in the form of a simple, yet effective device.

Although several embodiments have been illustrated and described, it will be obvious to those skilled in the art that various modifications may be made without departing from the spirit and scope of this invention.

What is claimed is:

1. Apparatus for positioning a sample vial, the vial having a rigid cap with a hole exposing a recessed septum to be pierced with a syringe needle for drawing a sample, said vial being loosely placed in a movable sample vial holder as used in automated sampling in analytical instruments, said apparatus comprising in combination: support means; a vial locator mounted on said support means; said locator having a body portion shaped to be engageable with the perimeter of the hole and to fit partially within the hole in the rigid cap of the vial; at least one of said vial holder and said support means being horizontally movable to position said body portion over said cap of the vial; said vial locator having a vertically extending guiding bore for receiving said syringe needle; resiliently biasing means for urging said body portion downwardly into engagement with the perimeter of the hole and to fit partially within the hole of the rigid cap of the vial to move said vial so that the guiding bore of the vial locator is in alignment with the hole in the vial cap to permit said syringe needle to move sequentially downwardly through said guiding bore, through said hole in the cap, and through said septum for drawing a sample from the sample vial; said support means includes a pivotally mounted arm on which said vial locator is mounted to be moved between a first position vertically above said vial holder, and a second position remote from said sample vial holder.

2. Apparatus according to claim 1 wherein said body portion is hemispherically shaped.

3. Apparatus according to claim 1 wherein said body portion is conically shaped.

4. Apparatus according to claim 3 wherein said cone has sides that are angled at about 45 degrees with respect to the axis of said bore.

5. Apparatus according to claim 1 wherein said biasing means are spring means.

6. Apparatus according to claim 1 wherein at least one of said sample vial holder and said vial locator is horizontally movable back and forth with respect to each other in successively decreasing increments while said biasing means are urging said body portion downwardly into engagement with the perimeter of the hole in said cap.

7. Apparatus according to claim 1 wherein said movable sample vial holder is a carousel; said carousel being horizontally rotatable back and forth through successively smaller incremental arcs while said biasing means are urging said body portion downwardly into engagement with the perimeter of the hole in said cap.

8. Apparatus according to claim 1 further comprising sensor means mounted on said support means adjacent said vial locator for detecting movement of said vial locator with respect to said support means.

9. A method for drawing a sample from a sample vial having a rigid cap with a hole exposing a recessed septum, said vial being loosely placed in a movable sample vial holder as used in automated sampling in analytical instruments comprising the steps of: horizontally positioning a vial locator, having a body portion shaped to be engageable with the perimeter of the hole and to fit partially within the hole in the rigid cap of the vial, over said cap of said sample vial; resiliently urging said body portion downwardly into engagement with the perimeter of the hole and partially within the hole of the rigid cap to move said vial so that a vertically extending guiding bore in the vial locator is in alignment with the hole in the vial cap; and thereafter sequentially passing a syringe needle through said vertically extending bore in the vial locator, through said hole in the cap, and through said septum for drawing the sample from the sample vial.

10. A method according to claim 9, further comprising the step of detecting the movement of said vial locator with detector means for controlling the operation of the instrument.

11. A method according to claim 9 further comprising the step of moving said sample vial holder with respect to said vial locator horizontally back and forth in successively decreasing increments during the step of resiliently urging the body portion downwardly into engagement with the perimeter of the hole in said vial cap.

* * * * *